United States Patent [19]

Katz et al.

[11] Patent Number: 4,735,803

[45] Date of Patent: Apr. 5, 1988

[54] REPELLING ANIMALS WITH COMPOSITIONS COMPRISING LEMON OIL AND ALPHA-TERPINYL METHYL ETHER

[75] Inventors: Ira Katz, Long Branch; Donald A. Withycombe, Lincroft, both of N.J.

[73] Assignee: International Flavors & Fragrances Inc., New York, N.Y.

[21] Appl. No.: 829,951

[22] Filed: Feb. 14, 1986

[51] Int. Cl.$^4$ .................... A61K 35/78; A61K 31/44
[52] U.S. Cl. ................... 424/195.1; 514/305; 514/715; 514/918; 514/920
[58] Field of Search ............. 424/195.1; 514/920, 514/918, 729, 305, 715

[56] References Cited

U.S. PATENT DOCUMENTS 4,255,460 3/1981 Mussinan et al. .............. 426/538
4,663,315 5/1987 Hasegawa et al. .............. 514/86

FOREIGN PATENT DOCUMENTS 0141266 5/1985 European Pat. Off. .

OTHER PUBLICATIONS

Chem. Abst. 103:183393t, 1985.
Chem. Abst. 103:155853z, 1985.
Chem. Abst. 97:145944y, 1982.

Primary Examiner—J. R. Brown
Assistant Examiner—John W. Rollins
Attorney, Agent, or Firm—Arthur L. Liberman

[57] ABSTRACT

Described are animal control compositions and methods; which compositions comprise lemon oil and α-terpinyl methyl ether taken alone or taken further together with quinine or salts thereof. The compositions can be used "as is" or in the form of a "controlled release" composition whereby the lemon oil and α-terpinyl methyl ether taken alone or further together with quinine or a salt thereof are intimately admixed (alone or with adjuvants including but not limited to other volatile, odorous ingredients) with a polymeric substance such as polyethylene in the form of pellets or functional articles, e.g., garbage bags.

6 Claims, 1 Drawing Sheet

REPELLING ANIMALS WITH COMPOSITIONS COMPRISING LEMON OIL AND ALPHA-TERPINYL METHYL ETHER

BACKGROUND OF THE INVENTION

This application relates to animal control compositions and methods, and more particularly relates to dog repellent compositions and to methods for repelling dogs.

It is frequently desired to exclude animals from certain areas. Such a need to limit the movements of animals ranges from controlling large and/or dangerous carnivores such as bears, wolves, coyotes and the like to controlling smaller animals such as rats, mice, squirrels and the like.

While the more undesirable animals, including most of those mentioned above, can be controlled by such direct methods as baiting and trapping, it is usually undesirable to deal with domestic animals so severely. This is particularly true of domesticated animals such as dogs which are pets and are generally allowed access to many areas in and around human habitation. It would be desirable to provide ways for excluding such domesticated animals from specific areas without otherwise materially limiting their freedom of movement.

In the past attempts have been made to control domestic animals through the use of materials which would be repellent to the particular animal and a number of animal repellent materials are known, for example, aliphatic or alicyclic ketones containing from about 6 up to about 20 carbon atoms in a suitable carrier as disclosed and claimed in U.S. Pat. No. 3,474,176 issued on Oct. 21, 1969. However, these prior art materials suffer from a number of deficiencies. Some of the materials are relatively ineffective and some of the more effective materials have unpleasant odors, in some cases such that they tend to be distasteful to humans, also. Other materials are so toxic that it is not possible to use them because of the possibility of accidental ingestion, either by the animals themselves or by humans.

Dog and cat repellent packaging materials are disclosed in Japanese published Patent Application (Kokai Tokkyo Koho No. 82/74,158 whereby polyolefin-paper packaging laminates were treated on the paper side with lemongrass oil for dog and cat repelling properties. For example, a polyethylene-kraft paper laminate was treated with a lemongrass oil emulsion and used for packaging food. This published Japanese Application is abstracted at Chem. Abstracts Vol. 97, No. 145944y.

German Offen. No. 1,248,361 published on Aug. 24, 1967 discloses an animal repellent consisting of formic acid, formaldehyde, butyric acid and ammonium sulfide and water. German Offen. No. 1,248,361 is abstracted at Chem. Abstracts Vol. 67, 1967 at 107669k.

Coyotes and dogs are indicated to be repelled by β-chloroacetyl chloride or cinnamaldehyde according to Lehner, et al, J. Wildl. Manage. 1976, 40 (1) pages 145–150, abstracted at Chem. Abstracts, Vol. 84, No. 175119g.

Japan Kokai No. 76/19,129 discloses the use of ethylthiometon or isothioate as a repellent for dogs, cats and birds. The Japan Kokai No. 76/19,129 is abstracted at Chem. Abstracts 85: 15377g.

German Offen. No. 2,525,686 published on Dec. 30, 1976 discloses a dog-repelling disinfectant composition containing pyridine, paraformaldehyde and formaldehyde. German Offen. No. 2,525,686 is abstracted at Chem. Abstracts, Vol. 86, No. 84765q.

Japan Kokai Tokkyo Koho No. 81/65,803 discloses the use of methyl nonyl ketone and/or methyl phenyl ketone and one or more of leaf aldehyde, leaf alcohol, cinnamic aldehyde and cinnamic alcohol as a repellent for dogs, cats and birds. Japan Kokai Tokkyo Koho No. 81/65,803 is abstracted at Chem. Abstracts 95: 75495k.

French Pat. No. 2,495,469 published on June 11, 1982 discloses a dog repellent containing 1.5% *Capsicum annum* ext. (Mombassa EW 810280 containing capsaicin as the active ingredient) and 98.5% hexanol. French Pat. No. 2,495,469 is abstracted at Chem. Abstracts Vol. 97 No. 118286c.

French Pat. No. 2,527,902 published on Oct. 9, 1983 discloses the use of fennel seed and ethanol taken together with copper sulfate and ammonia as a dog repellent. French Pat. No. 2,527,902 is abstracted at Chem. Abstracts, Vol. 100, No. 134333c.

French Pat. No. 2,542,002 discloses adding terpenes (optionally halogenated), terpene alcohols and/or terpene esters to plastics, especially polyethylene garbage bags, thereby causing them to be free of unpleasant smells even when filled with malodorous materials, and to be avoided by animals. French Pat. No. 2,542,002 indicates that garbage bags prepared from this film and filled with kitchen wastes were not attacked by dogs, cats or rats, while those prepared without the terpenes were so attacked. French Pat. No. 2,542,002 is abstracted at Chem. Abstracts, Vol. 102, No. 7726z.

French Pat. No. 2,538,222 published on June 29, 1984 discloses a dog repellent comprising fennel oil, copper sulfate, ammonia and water. French Pat. No. 2,538,222 is abstracted at Chem. Abstracts, Vol. 102, No. 41601q.

French Pat. No. 2,546,718 published on Dec. 7, 1984 discloses a cat and dog repellent composition containing fennel oil, marjoram oil, rosemary oil, copper sulfate, ammonia and water. French Pat. No. 2,546,718 is abstracted at Chem. Abstracts, Vol. 102, No. 199618k.

Nothing in the prior art, however, discloses the unobvious, unexpected and advantageous properties of the composition of matter of our invention containing lemon oil and α-terpinyl methyl ether having the structure:

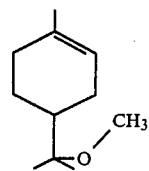

and, optionally, quinine having the structure:

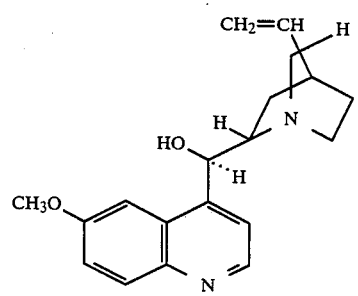

or one or more salts thereof.

U.S. Pat. No. 4,173,543 issued on Nov. 6, 1979 (assigned to the assignee of the instant application, International Flavors & Fragrances Inc.) and U.S. Pat. No. 4,255,460 issued on Mar. 10, 1981 (assigned to the assignee of the instant application, International Flavors & Fragrances Inc.) each disclose the use of the compound α-terpinyl methyl ether having the structure:

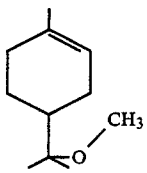

for its organoleptic properties.

These patents also disclose, for use as food flavorants, the combination of the α-terpinyl methyl ether with one or more of hundreds of compounds including, inter alia, lemon essential oil (see line 53, column 13 of 4,255,460 and line 12 column 15 of U.S. Pat. No. 4,173,543). Nothing in either of U.S. Pat. Nos. 4,255,460 or 4,173,543 infers or expressly discloses the use of lemon essential oil taken together with the compound having the structure:

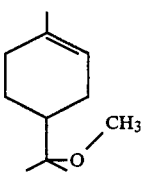

in repelling dogs or other mammalian species.

DETAILED DESCRIPTION OF THE DRAWINGS

Figure 1:
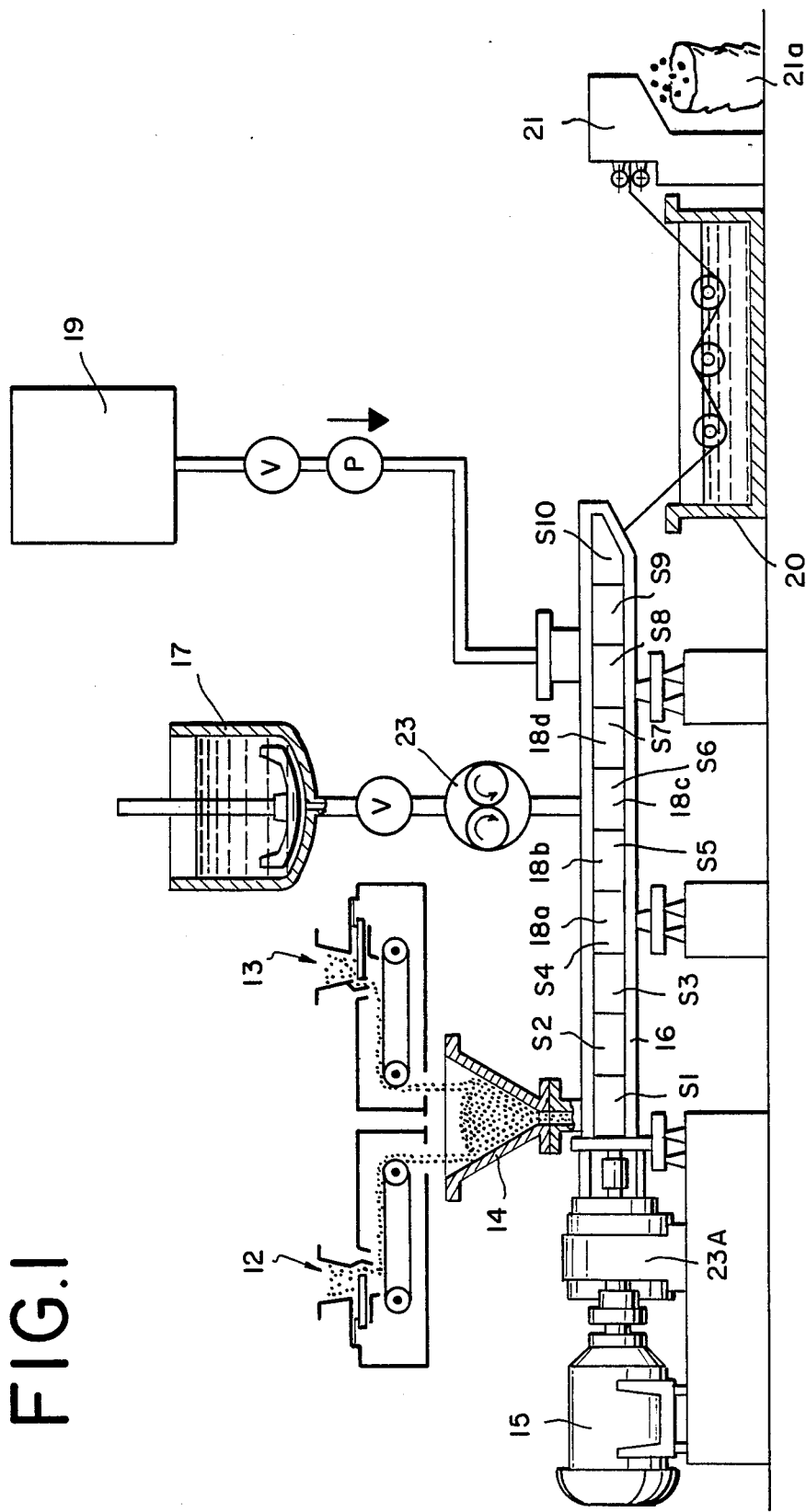
FIG. 1 is a cutaway side elevation schematic diagram of a screw extruder during the compounding of a resin with the fluidized animal repellent composition of matter of our invention containing lemon essential oil and α-terpinyl methyl ether and incorporates pelletizing apparatus used in pelletizing the extruded composition of matter so produced as a result of the extrusion operation.

FIG. 1 is a schematic cutaway elevation diagram of the extrusion pelletizing apparatus useful in carrying out a process whereby the animal repellent composition of our invention, the composition comprising lemon essential oil and α-terpinyl methyl ether taken alone or further together with quinine or one or more of its salts is incorporated into a polymer for a subsequent formation of functional articles containing such a composition. Motor 15 drives the extruder screws located at 23A and barrel 16, the extruder being operated at temperatures in the range of from about 150° C. up to about 250° C. At the beginning of the barrel, resin at source 12 together with additives, e.g., opacifiers, processing aids, colors, pearlescent agents and densifiers at location 13 is added via addition funnel 14 into the extruder. Simultaneously (when the operation reaches "steady state") the animal repellent material which comprises lemon essential oil and α-terpinyl methyl ether taken alone or taken further together with quinine or one or more of its salts is added to the extruder at one, two or more of barrel segments 3-8 (shown as S3, S4, S5, S6, S7 and S8) of the extruder (which may be a twin screw or single screw extruder) at locations 18a, 18b, 18c and 18d by means of gear pump 23 from source 17. From source 19 into barrel segments 5-10 (shown as S3, S4, S5, S6, S7 and S8), optionally, a gaseous or liquid blowing agent, e.g., nitrogen, carbon dioxide and the like, are added simultaneously with the addition of the animal repellent material. The feed range of resin is about 80-300 lbs. per hour. The feed rate range of the animal repellent composition comprising the lemon essential oil and α-terpinyl methyl ether taken alone or further together with quinine or one or more of its salts is between 1 and 35% of the feed rate range or the resin. The blowing agent rate range is such that the pressure of the gas or the pressure over the liquid being fed into the extruder is between about 50 and 200 psig. If desired, the extruded ribbon or cylinder may be passed through water bath 20 and pelletizer 21 into collection apparatus 21a. A detailed description of the operation of this apparatus is disclosed in U.S. Pat. No. 4,521,541 issued on June 4, 1985, the specification for which is incorporated by reference herein.

THE INVENTION

The invention comprises the novel compositions and component mixtures comprised in such compositions as well as the novel methods and steps of methods, specific embodiments of which are described hereinafter by way of example only and in accordance with what is now considered the preferred manner of practicing this invention.

Briefly, the compositions of this invention comprise a suitable carrier and:

(a) from about 1 part by weight up to about 9 parts by weight of α-terpinyl methyl ether having the structure:

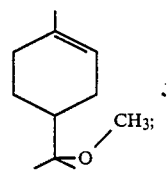

(b) from about 9 parts by weight down to about 1 part by weight of lemon essential oil as hereinafter defined; and optionally (c) from about 0.05 parts by weight up to about 5 parts by weight of quinine having the structure:

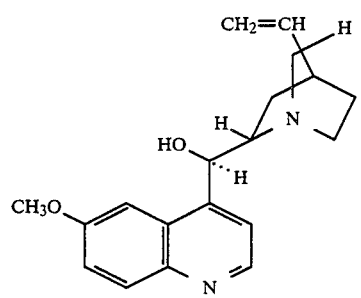

or one or more of its salts and, optionally, adjuvants including but not limited to other volatile, odorous ingredients.

It is preferred that the quinine or one or more of its salts be in solution.

The lemon essential oil/α-terpinyl methyl ether compositions (taken alone or further together with quinine or one or more of its salts) are present in the overall composition in amounts effective to repel animals, preferably dogs, from the area in which the compositions are applied. The method of this invention comprises treating an article or an area with the lemon essential oil/α-terpinyl methyl ether composition (taken alone or further together with quinine or one or more of its salts) to repel animals from the treated area. Unless otherwise indicated, all parts, proportions, percentages and ratios herein are by weight.

Some compositions of this invention have been found to be especially adapted for use in pressurized aerosol dispensing containers. Accordingly, in certain embodiments of this invention, the composition comprises the α-terpinyl methyl ether/lemon essential composition (taken alone or further together with quinine or one or more of its salts), a propellent and generally a vehicle for the α-terpinyl methyl ether/lemon essential oil composition (taken alone or further together with quinine or one or more of its salts). Such compositions are very conveniently and economically dispensed from aerosol containers and rapidly produce the desired repellent action in the area sprayed.

Furthermore, the α-terpinyl methyl ether/lemon essential oil composition (taken alone or further together with quinine or one or more of its salts) can be incorporated into a polymer such as polyethylene by standard techniques such as that disclosed in U.S. Pat. No. 4,521,541 issued on June 4, 1985, the disclosure for which is incorporated by reference herein; or by means of the technique set forth in U.S. Pat. No. 3,505,432 which discloses a method of incorporating a volatile material into a polyolefin which comprises:

(a) mixing a first amount of liquid polyolefin, e.g., polyethylene or polypropylene with a relatively large amount of volatile material to form a flowable mass;

(b) forming drops from said mass and causing substantially instantaneous solidification of said drops into polyolefin pellets having a relatively large amount of volatile material (e.g., the α-terpinyl methyl ether/lemon essential oil composition taken alone or further together with quinone or one or more of its salts, this composition taken alone or further together with additional adjuvants including but not limited to other volatile, odorous ingredients) imprisoned therein;

(c) melting said pellets with a second amount of said polyolefin, said second amount being larger than said first amount; and (d) solidifying the melt of "(c)".

The articles disclosed in U.S. Pat. No. 4,247,498 issued on Jan. 27, 1981 are useful in conjunction with our invention. U.S. Pat. No. 4,247,498 discloses microporous polymers which are capable of containing volatile substances which we have discovered can be the lemon essential oil/α-terpinyl methyl ether composition (taken alone or further together with quinine or one or more of its salts) of our invention in forms ranging from films to blocks in intricate shapes, from synthetic thermoplastic polymers such as olefinic condensation or oxidation polymers. In one embodiment of U.S. Pat. No. 4,247,498 the microporous polymers are characterized by relatively homogeneous three dimensional cellular structures having cells connected by pores of smaller dimensions. Also disclosed in U.S. Pat. No. 4,247,498 is a process for making microporous polymers from such thermoplastic polymers by heating a mixture of polymer and a compatible liquid (e.g., a volatile substance which could include the α-terpinyl methyl ether/lemon essential oil composition taken alone or further together with quinine or one or more of its salts of our invention) to form a homogeneous solution, cooling said solution under non-equilibrium thermodynamic conditions to initiate liquid-liqiuid phase separation, and continuing said cooling until the mixture achieves a substantial handling strength. Also disclosed in said U.S. Pat. No. 4,247,498 are microporous polymer products which contain relatively large amounts of such functionally useful fluids as animal repellent compositions, e.g., the α-terpinyl methyl ether/lemon essential oil composition (taken alone or further together with quinine or one or more of its salts) of our invention, and behave as solids. The effective repellent substances are mixtures of α-terpinyl methyl ether having the structure:

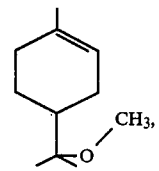

lemon essential oil as further defined, infra, and, optionally, quinine having the structure:

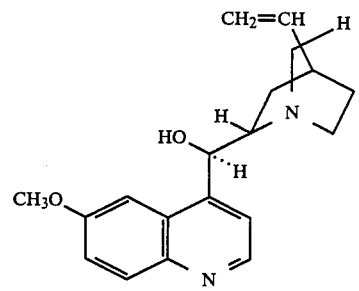

or one or more of its salts in the proportion ranges as set forth, supra.

The α-terpinyl methyl ether useful in the conjunction with the practice of our invention, may be produced according to the method of Royals, J. Am. Chem. Soc., 71, 2568–71, (1949) the disclosure of which is incorporated by reference herein. Such disclosure is also set forth together with spectra in Example X at lines 37–60, column 26 of U.S. Pat. No. 4,173,543 issued on Nov. 6, 1979, the specification for which is incorporated by reference herein.

It will be understood herein that the α-terpinyl methyl ether as well as the lemon essential oil and the quinine (or one or more of its salts) of our invention can be used either pure or in commercially available form. They can also be used in admixture with an acceptable solvent, e.g., food grade ethyl alcohol.

Other carriers for the use of this invention can be selected from a wide group of liquid and solid materials suitable for applying the α-terpinyl methyl ether/lemon essential oil compositions (taken alone or further together with quinine or one or more of its salts) of matter of this invention to an area or to an article of manufacture, e.g., a garbage bag. The α-terpinyl methyl ether/lemon essential oil compositions (taken alone or further together with quinine or one or more of its salts) can be conveniently applied, for example, to an article (e.g., in the interstices of polymeric garbage bags), to an area in the form of solutions or emulsions, or adsorbed or absorbed on solid materials, desirably finely divided solid materials such as dust, powders and the like, for example, attapulgite clay, bentonite clay, fuller's earth, diatomaceous earth, vermiculite, ground corn cob and kaolin.

In addition to ethyl alcohol, for liquid compositions, a wide variety of solvents can be used with the α-terpinyl methyl ether/lemon essential oil compositions of matter (taken alone or further together with quinine or one or more of its salts) of our invention. For example, solvents such as hexane, kerosene, petroleum distillates and the like (including aromatic hydrocarbons and other aromatic petroleum-based materials) and oxygenated hydrocarbons, desirably alcohols (including the ethanol cited, supra) and ketones such as methanol, ethanol, isopropanol, acetone, methyl isobutyl ketone, methyl ethyl ketone, and the like are satisfactory solvents. It is preferred that the solvent be essentially odorless or have a mild, pleasant odor. Generally, the amount of α-terpinyl methyl ether/lemon essential oil (taken alone or further together with quinine or one or more of its salts) in the carrier ranges from about 0.25% up to about 10% by weight and preferably from about 0.5% up to about 5%.

Liquids in which the α-terpinyl methyl ester/lemon essential oil compositions (taken alone or further together with quinine or one or more of its salts) of our invention are insoluble or only sparingly soluble can also be used in the preparation of compositions of this invention. Such liquids will also be referred to from time to time herein as "non-solvents". In such case the composition is in the form of an emulsion or dispersion of the α-terpinyl methyl ether/lemon essential oil (taken alone or further together with quinine or one or more of its salts) in the non-solvent. Water is a preferred liquid because it is odorless, non-toxic and readily compatible with the α-terpinyl methyl ether/lemon essential oil compositions of matter (taken alone or further together with quinine or one or more of its salts) of our invention, and the surfaces to which such α-terpinyl methyl ether/lemon essential oil compositions (taken alone or further together with quinine or one or more of its salts) are generally applied.

Such non-solvent containing or aqueous compositions can contain surface active agents such as emulsifiers to disperse or emulsify the α-terpinyl methyl ether/lemon essential oil composition (taken alone or further together with quinine or one or more of its salts) in the water or other liquid in which the α-terpinyl methyl ether/lemon essential oil composition (taken alone or further together with quinine or one or more of its salts) is insoluble or in which the α-terpinyl methyl ether/lemon essential oil composition (taken alone or further together with quinine or one or more of its salts) of our invention has only limited solubility. Examples of such surface active agents are alkylarylpolyether alcohols, sodium polyglycolether sulfonates, purified sodium lignosulfonate, sodium lauryl alcohol sulfate and the like.

Within the contemplation of our invention are concentrates suited for dispersion in water to prepare sprayable emulsions. Such concentrations contain a relatively large quantity of the α-terpinyl methyl ether/lemon essential oil composition of matter (taken alone or further together with quinine or one or more of its salts) of our invention, a small quantity of an emulsifier sufficient to disperse the material in the non-solvent and an organic solvent of the class described above for the α-terpinyl methyl ether/lemon essential oil composition of matter (taken alone or further together with quinine or one or more of its salts). Such concentrates desirably contain from about 20% up to about 60% of the α-terpinyl methyl ether/lemon essential oil composition of matter (taken alone or further together with quinine or one or more of its salts) and from about 2% up to about 10% of the surface active agent, the remainder being the organic solvent. Such concentrates are conveniently diluted with from about 4 up to about 99 parts of water for each part of concentrate.

In certain preferred embodiments of this invention it has been found that the α-terpinyl methyl ether/lemon essential oil compositions of matter (taken alone or further together with quinine or one or more of its salts) of our invention are especially adapted for application from aerosol type spray cans in conjunction with a self-propellant composition. Such self-propellant compositions are especially effective in dispersing the α-terpinyl methyl ether/lemon essential oil (taken alone or further together with quinine or one or more of its salts) compositions in the desired area or on or in the desired article (e.g., garbage bag) and in controlling animals by repelling them from such sprayed area or sprayed article of manufacture. While it is possible to use liquids such as water in conjunction with the surface active agent for the self-propellant compositions, it is preferred that the self-propellant aerosol composition of this invention comprise the α-terpinyl methyl ether/lemon essential oil composition (taken alone or further together with quinine or one or more of its salts) of our invention, a propellant agent and usually a solvent carrier for the α-terpinyl methyl ether/lemon essential oil composition (taken alone or further together with quinine or one or more of its salts). The solvents used for the α-terpinyl methyl ether/lemon essential oil composition ((taken alone or further together with quinine or one or more of its salts) of our invention are as set forth, supra. The propellant can be any of the aerosol types including lower hydrocarbons such as propane and isobutane, gaseous materials such as carbon dioxide, and the like, or the halogenated hydrocarbons such as dichlorodifluoromethane, dichlorotetrafluoroethane, chlorotrifluoromethane, dichlorofluoromethane and the like. It is preferred in practicing our invention to utilize lower hydrocarbon and carbon dioxide as propellant agents.

It will be understood that where the propellant agent is a solvent for the α-terpinyl methyl ether/lemon essential oil composition (taken alone or further together with quinine or one or more of its salts) of our invention, it can act in this dual capacity and no further solvent will be necessary. The self-propellant compositions of this invention will generally contain from about 0.5 up to about 25% of the α-terpinyl methyl ether/lemon essential oil composition (taken alone or further together with quinine or one or more of its salts) of our invention and from about 2 up to about 50% of the propellant agent, the remainder being solvent or non-solvent plus emulsifier. Generally, it is preferred that the amount of α-terpinyl methyl ether/lemon essential oil composition (taken alone or further together with quinine or one or more of its salts) of our invention be in the range of from about 1 up to about 10% of the self-propellant composition, since lower concentrations α-terpinyl methyl ether/lemon essential oil composition (taken alone or further together with quinine or one or more of its salts) require that the area be very heavily sprayed to obtain the desired repellent activity. On the other hand, if the composition is too concentrated with respect to the α-terpinyl methyl ether/lemon essential oil (taken alone or further together with quinine or one or more of its salts) of our invention, the spray will be difficult to control and will result in wasteful over-application of α-terpinyl methyl ether/lemon essential oil composition of matter (taken alone or further together with quinine or one or more of its salts) to the area.

It will be understood that the carriers for use herein can also comprise amounts of other adjuvant materials and inert ingredients. For example, the compositions of our invention can also contain other volatile odorants (including perfumes), coloring agents such as dyes and pigments and the like. It is also possible to admix the active ingredients for other purposes with the carrier including, for example, miticides such as methoxychlor, insecticides such as DDT, DDE, dieldrin and malathion, other animal repellents, and insect repellents. For example, a composition can be specially prepared for use on bushes which contains insecticidal or other agents so that the bushes can be made repellent to domestic animals (e.g., dogs) and treated for other conditions at the same time. Thus, an evergreen bush or shrub could be sprayed with the composition of our invention wherein the carrier contains an insecticide so that the composition would repel dogs and protect the plant against red spider mites at the same time. Further, if desired, all or part of the α-terpinyl methyl ether/lemon essential oil composition (taken alone or further together with quinine or one or more of its salts) of our invention can be encapsulated by well known techniques to provide for controlled release over a relatively long period of time such as, for example, using the techniques set forth in U.S. Pat. No. 3,971,852 issued on July 27, 1976 (Brenner, et al) entitled "PROCESS OF ENCAPSULATING AN OIL AND PRODUCED THEREBY", the specification for which is incorporated by reference herein.

The following examples are given to illustrate preferred embodiments of this invention as it is now preferred to practice it. It will be understood that these examples are illustrative and the invention is not to be considered as restricted thereto except as indicated in the appended claims.

In all examples set forth, infra, the test methods used are taken from "Test Methods For Vertebrate Pest Control And Management Materials", a symposium sponsored by ASTM, Committee E-35 on Pesticides (*AMERCIAN SOCIETY FOR TESTING AND MATERIALS,* Monterey, Calif., Mar. 8, 1976 (ASTM Special Technical Publication 625 by W. B. Jackson and R. E. Marsh)) [American Society For Testing and Materials, 1916 Race Street, Philadelphia, Pa. 19103]; article published therein at page 123 by C. C. Snider and J. A. McCann entitled "Proposed Efficacy Test for Aerosol Dog Repellents that Are Designed to Reduce Damage to Garbage Bags".

More specifically, in each of the examples set forth, infra, the Snider and McCann Efficacy Test was designed to provide data to support a claim that the given material can reduce damage to garbage bags to a greater extent than a second given material.

A minimum of eight dogs are tested individually within rectangular arenas for one hour on each of four days. Three garbage bags are placed at each end of each arena. The bags at one end of the arenas are treated with the repellent to be tested (in this case mixtures of α-terpinyl methyl ether and a given lemon essential oil or mixtures of α-terpinyl methyl ether, a given lemon essential oil and quinine) (referred to as "treated bags A") and those at the other end are treated with a known prior art commercially available repellent, e.g., methyl nonyl ketone (referred to as "treated bags B"). The bags are appropriately sprayed and stored for the maximum length of time (prior to testing) for which efficacy is desired to be claimed. The amount of ration placed in each bag is calculated to give the dog one third of an "adequate" amount of nutrients. Consequently, the dog receives free choice between "treated bags A" and "treated bags B" and is not forced by hunger to open any of the "treated bags A". The damage to a bag is recorded as "opened" or "unopened". Dogs are divided into groups of four and a four by four Graeco-Latin square containing days, arenas, dogs and point of introduction into the arenas is constructed for each group. Percent repellency is calculated for each day, each dog, and the total test. Reference tests using six untreated bags are employed as checks on the activity of the dogs in repellent tests.

The Snider and McCann article entitled "Proposed Efficacy Test for Aerosol Dog Repellents that Are Designed to Reduce Damage to Garbage Bags" is incorporated by reference herein.

In the instant specification and throughout the following examples the term "lemon essential oil" is intended to mean "oil of lemon" having an origin in citrus limon and termed "oleum limonis" as defined on pages 81–115, inclusive, of "The Essential Oils" by Ernest Guenther, Vol. 3, published by Robert E. Krieger Publishing Co., Box 542, Huntington, N.Y. 11743 (reprint, 1974); original edition 1949, published by Van Nostrand Reinhold Co., 1949, including, but not limited to:
(i) California Lemon Oil;
(ii) Italian Lemon Oil;
(iii) Terpeneless Italian Lemon Oil;
(iv) Sesquiterpeneless Italian Lemon Oil;
(v) Brazilian Lemon Oil; and
(vi) Israel Lemon Oil,
each of which contains materials selected from the group consisting of
(i) α-Pinene;
(ii) Camphene;
(iii) β-Pinene;
(iv) Phellandrene;
(v) Methyl heptenone;
(vi) Gamma-Terpinene;
(vii) d-Limonene;
(viii) Octaldehyde;
(ix) Citronellol;
(x) α-Terpineol;
(xi) Citral;
(xii) Linalyl acetate;
(xiii) Geraniol;
(xiv) Geranyl acetate;
(xv) Nerol;

(xvi) Neryl acetate;
(xvii) Citronellol;
(xviii) Citronellyl acetate;
(xix) Bisabolene;
(xx) Cadinene;
(xxi) Acetic acid;
(xxii) Capric acid;
(xxiii) Lauric acid;
(xxiv) Methyl anthranilate;
(xxv) Limettin; and
(xxvi) Linalool.

The Italian Lemon Oils include but are not limited to:
Sfumatrici (Andnonaco);
Sfumatrici (Morasco);
Sfumatrici (Cannavo);
Peratoner (Process: Distilled);
Rotary Rasping (Centrifuged);
Cannavo (Whole Fruit);
Speciale (Whole Fruit);
Speciale (Bennett-Cusmano Process);
Avena (Whole Fruit);
Avena (Bennett-Cusmano Process); and
Sponge The disclosure of the Guenther reference cited, supra, is incorporated herein by reference.

EXAMPLE I

A. The following composition is prepared:

| INGREDIENTS | PARTS BY WEIGHT |
|---|---|
| α-Terpinyl methyl ether | 2.00 |
| Lemon essential oil | 8.00 |
| (Sponge; Cannavo Machine) | |
| [Specific Gravity at | |
| 15.5°: 0.8593; | |
| Optical Rotation | |
| at 15.5°: +59° 23'; | |
| Citral Content: 3.75% | |
| Ester Content: 3.10% | |
| Non-volatile Residue: 4.96%] | |

The resulting product is placed in a blown film at the rate of 1% using the technique as set forth in U.S. Pat. No. 4,521,541 issued on June 4, 1985. The foregoing composition is compared with methyl nonyl ketone and the results are as follows:

| INGREDIENTS | OPEN BAGS | CLOSED BAGS | TOTAL BAGS |
|---|---|---|---|
| Composition of matter containing α-terpinyl methyl ether and lemon essential oil | 9 | 15 | 24 |
| Methyl nonyl ketone | 21 | 3 | 24 |
| TOTAL | 30 | 18 | 48 |

CHI-SQUARE = 10.75556; degrees of freedom = 1
95% Confidence limits: 1.974255E-02 and 0.4359145
ODDS RATIO = 8.571429E-02; p = 1.039624E-03

EXAMPLE II

Using the apparatus of FIG. 1, at the rate of 1% the following composition is placed in polyethylene and a blown film is produced and formed into garbage bags:

| INGREDIENTS | PARTS BY WEIGHT |
|---|---|
| Quinine having the structure: | 1.00 |
| in food grade ethanol (50%) | |
| α-Terpinyl methyl ether having the structure: | 2.98 |
| Lemon essential oil | 15.92 |
| (Sponge; Cannavo Machine) | |
| [Specific Gravity at | |
| 15.5°: 0.8593; | |
| Optical Rotation | |
| at 15.5°: +59° 23'; | |
| Citral Content: 3.75% | |
| Ester Content: 3.10% | |
| Non-volatile Residue: 4.96%] | |

Tests according to the procedure set forth on page 24, supra, were carried out and the following results (Chi-Square) occurred:

| INGREDIENT | OPEN BAGS | CLOSED BAGS | TOTAL BAGS |
|---|---|---|---|
| Mixture of quinine, lemon essential oil and α-terpinyl methyl ether | 15 | 33 | 48 |
| Methyl nonyl ketone | 30 | 18 | 48 |
| TOTAL | 45 | 51 | 96 |

Degrees of Freedom = 1
CHI-SQUARE = 8.19; p = 4.192233E-03
ODDS RATIO = 0.2727273
95% Confidence limits: 0.1066814 and 0.687878

EXAMPLE III (Control Example)

At the rate of 1% using the apparatus of FIG. 1, lemon essential oil (Sponge; Cannavo Machine [Specific Gravity at 15.5°: 0.8593; Optical Rotation at 15.5°: +59° 23'; Citral Content: 3.75%; Ester Content: 3.10%; Non-volatile Residue: 4.96%]) was added to polyethylene film and a blown film was produced and formed into garbage bags. Garbage bags were also produced with methyl nonyl ketone and compared using the aforementioned procedure. The results are as follows:

| INGREDIENT | OPEN BAGS | CLOSED BAGS | TOTAL BAGS |
|---|---|---|---|
| Lemon essential oil (Sponge; Cannavo Machine [Specific Gravity at 15.5°: 0.8593; Optical Rotation at 15.5°: +59° 23'; Citral Content: 3.75% Ester Content: 3.10% Non-volatile Residue: 4.96%]) | 13 | 11 | 24 |
| Methyl nonyl ketone | 6 | 18 | 24 |
| TOTAL | 19 | 29 | 48 |

Degrees of Freedom = 1
CHI-SQUARE = 3.136116; p = 7.657588E-02
ODDS RATIO = 3.545455
95% Confidence limits: 0.8948058 and 14.63906

The results of the foregoing experiments prove that α-terpinyl methyl ether taken together with lemon essential oil alone or taken further together with quinine has unexpected, unobvious and advantageous properties as an animal repellent.

What is claimed is:

1. A composition of matter consisting essentially of lemon essential oil, alpha-terpinyl methyl ether having the structure:

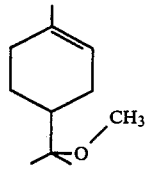

with the weight ratio range of lemon essential oil:alpha-terpinyl methyl ether being from about 1:9 up to about 9:1 and having added thereto quinine having the structure:

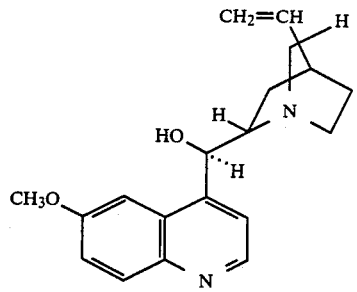

or one or more of its salts.

2. An article of manufacture comprising a shaped polymer and intimately admixed therewith the composition of matter of claim 1.

3. An article of manufacture comprising a polymer and intimately admixed with said polymer a composition of matter consisting essentially of lemon essential oil and alpha-terpinyl methyl ether having the structure:

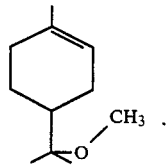

with the weight ratio of lemon essential oil:alpha-terpinyl methyl ether being from about 1:9 up to about 9:1.

4. A method for repelling animals which comprises exposing an animal to a repellent amount of the composition of claim 1.

5. A method for repelling animals which comprises exposing an animal to the article of manufacture defined according to claim 3.

6. A method for repelling animals which comprises exposing an animal to the article of manufacture of claim 2.

* * * * *